United States Patent
Maksimovich

(10) Patent No.: US 7,490,612 B2
(45) Date of Patent: Feb. 17, 2009

(54) METHOD OF TRANSLUMINAL LASER REVASCULARIZATION OF CEREBRAL BLOOD VESSELS HAVING ATHEROSCLEROTIC LESIONS

(76) Inventor: Ivan Vasilievich Maksimovich, 121248, 4/2 Moscow, Kutuzovsky Prospect, Apt. 121, Moscow (RU) 121248

( * ) Notice: Subject to any disclaimer, the term of this patent is extended or adjusted under 35 U.S.C. 154(b) by 182 days.

(21) Appl. No.: 11/698,846

(22) Filed: Jan. 29, 2007

(65) Prior Publication Data

US 2007/0191820 A1    Aug. 16, 2007

(30) Foreign Application Priority Data

Feb. 13, 2006    (RU) .............................. 2006104137

(51) Int. Cl.
*A61B 19/00*    (2006.01)

(52) U.S. Cl. .............................. 128/898; 606/7; 606/15

(58) Field of Classification Search ................. 128/898; 606/7, 10–18; 607/88, 89, 92; 604/164.01, 604/171, 174

See application file for complete search history.

(56) References Cited

U.S. PATENT DOCUMENTS

| 5,041,108 | A |   | 8/1991  | Fox et al.              |
|-----------|---|---|---------|-------------------------|
| 5,846,220 | A | * | 12/1998 | Elsberry ......... 604/500 |
| 5,895,378 | A | * | 4/1999  | Nita ............. 604/529 |
| 6,117,128 | A | * | 9/2000  | Gregory .............. 606/7 |
| 6,814,962 | B1|   | 11/2004 | Benoit et al.           |
| 6,962,585 | B2|   | 11/2005 | Poleo, Jr.              |
| 7,189,222 | B2| * | 3/2007  | Elsberry ......... 604/506 |

FOREIGN PATENT DOCUMENTS

| DE | 10351949 | 6/2005 |
| SU |   897251 | 1/1982 |
| SU |  1722504 | 3/1992 |

* cited by examiner

*Primary Examiner*—Ahmed M Farah

(57) ABSTRACT

A method of transluminal laser revascularization of cerebral blood vessels having atherosclerotic lesions by introducing into the affected lumen a microcatheter device composed of a plurality of coaxial microcatheters moveably inserted one into the other and guiding through the catheters a laser-powered lightguide optical fiber, the end face of which is positioned at an optimal distance from the occlusive tissues which are then deteriorated by laser radiation at a relatively high laser power from 20 to 35 W.

18 Claims, No Drawings

METHOD OF TRANSLUMINAL LASER REVASCULARIZATION OF CEREBRAL BLOOD VESSELS HAVING ATHEROSCLEROTIC LESIONS

CROSS-REFERENCE TO RELATED APPLICATIONS

The present patent application is related to pending U.S. patent application Ser. No. Ser. No. 11/650,346 filed by the same applicant on Jan. 8, 2007 and titled "Method and Device for Endovascular Treatment of Alzheimer's Disease."

FIELD OF THE INVENTION

The present invention relates to the field of medicine, neuroangiology, and more specifically, to a method of transluminal laser revascularization of cerebral blood vessels having atherosclerotic lesions.

BACKGROUND OF THE INVENTION

To better understand the principle of the invention, it would be advantageous to define in a simple way some terminology that relates to the field of treatment of cerebral artery diseases.

Arterial Supply: Blood is supplied to the brain by three major artery systems: the right and left internal carotid arteries and the vertebral/basilar system. The carotid arteries supply the anterior two-thirds of the cerebral hemispheres, and the vertebral/basilar system supplies the brainstem and cerebellum and posterior parts of the hemispheres.

Carotid Arteries: As the internal carotid arteries travel upward through each hemisphere, they divide into two branches, the anterior and middle cerebral arteries. The anterior cerebral artery supplies the inferior surface of the frontal lobe and the medial parts of the hemisphere. The middle cerebral artery supplies the basal ganglia, deep white matter, and the lateral surface of the hemisphere. The basal ganglia are supplied by small branches of the middle cerebral artery called the lenticulostriatal arteries.

Vertebral/Basilar System: The vertebral arteries run upward through the cervical vertebrae of the neck and enter the skull through the foramen magnum. The two vertebral arteries join and form the basilar artery, which supplies the pons, cerebellum, and midbrain. As the basilar artery reaches the top of the cerebellum, it divides to form two posterior cerebral arteries. These arteries supply the thalamus, medial surface of the temporal lobes, and virtually the entire occipital lobes.

Venous Flow: Blood drains from the brain through shallow and deep systems of venous flow. The surfaces of the hemispheres are drained by superficial veins that flow into the superior sagittal sinus. The inferior surface of the brain and deep structures are drained by a system that eventually forms the straight sinus. The straight and superior sinuses in the posterior part of the brain join to eventually form the jugular veins in the neck.

Stroke (Cerebral Vascular Accident [CVA]): Stroke is a general term used to describe virtually any disturbance in cerebral circulation that results in ischemia and anoxia. Another term commonly employed is cerebral vascular accident (CVA). These disturbances include occlusion of the arteries by fatty emboli or blood clots, breaks in arteries that produce hemorrhage, and ischemia resulting from decreased blood pressure and overall perfusion.

Ischemia: Deficiency of oxygen in a tissue due to obstruction of a blood vessel, causing temporary damage to living cells due to insufficient blood supply.

Atherosclerosis represents the most common mechanism producing focal ischemia. According to the American Heart Association, coronary atherosclerosis is the term for the buildup of fatty substances, cholesterol, cellular waste products, calcium and fibrin (a clotting material in the blood) in the inner lining of an artery. The buildup that results is called plaque. The sclerotic plaque lines the artery walls and builds up over the course of many years. The plaque buildup may eventually reduce arterial flow, completely block the artery, or produce an embolus that flows in the arterial stream to block an artery downstream. Other sources include infection emboli and emboli produced by cardiac disease. Once an artery is occluded, neurons perfused by the artery no longer receive necessary nutrients and oxygen. These cells eventually die, and this results in a focal infarct. The area appears hypodense on neuroimaging, and autopsy reveals a fluid-filled cavity.

Several methods exist for the revascularization of cerebral blood vessels having atherosclerotic lesions. Patients with certain types of coronary insufficiencies documented by certain coronary angiographic findings may be helped symptomatically by coronary artery bypass operations. Other patients sometimes may benefit from other types of arterial surgery, for example, various bypass operations, or endarterectomies, which surgically attempt recanalization of certain occluded blood vessels. These are generally patients with severe disease but yet who meet certain diagnostic criteria and who are healthy enough to undergo what amounts to major surgery with relatively high morbidity and mortality rates. The cost is immense for many of these operations and incumbent hospitalization, including expensive special equipment that is required and special training that is necessary for a team to use the special surgical equipment.

For example, it is estimated that a single coronary bypass operation may cost a patient over $50,000, including hospitalization fees and surgical fees. Availability of this special type of surgery for vascular problems is limited. Long-term efficacy of coronary bypass surgery is as yet unknown, and the appropriate diagnostic and surgical criteria remain controversial.

Attempts have been made to solve the above problems by means of various innovative methods and devices. For example, Russian Patent SU 897251 disclosed in 1982 (inventor I. N. Danilova) describes a method of treating patients suffering from cerebral atherosclerosis with ischemic stroke in the earlier rehabilitation period by introducing 1 to 2% aminalon solution on a daily basis by means of endonasal electrophoresis with gradual increase in the current density from 0.01-0.02 to 0.02-0.03 $mA/cm^2$. The first three to four procedures are carried out for 5 minutes, with 3- to 5-min. intervals between procedures, while duration of subsequent procedures is gradually increased to 15 to 30 minutes. Tests on 53 patients showed that such treatment made it possible to shorten duration of treatment from 1.5 to 3 months to 20 to 25 days.

Russian Patent SU 1722504 disclosed in 1992 (inventor V. I. Fomichov, et al) describes a method for shortening the duration of treating atherosclerosis of coronary blood vessels by means of plasma-absorption introduced in three procedures in an amount of 1000 to 1200 ml during 90 to 120 minutes with 2- to 5-minute intervals between procedures.

German Patent DE 10351949 issued in 2005 to M. Strobl, et al., discloses a method of treating atherosclerosis of coronary blood vessels by using an aneurism stent, e.g., for the widening of intracerebral vessels. The aneurysm stent consists of a container and a stretched structure with a range having changed blood permeability with stretcher structure being tubular and expandable within container which can therefore be partly supported.

U.S. Pat. No. 6,814,962 issued in 2004 to P. Benoit, et al., discloses recombinant viruses and their use in treating atherosclerosis and other forms of coronary artery disease and a method, reagent, and kit for evaluating susceptibility to same. The aforementioned recombinant viruses comprise heterologous DNA sequence coding for a lipase involved in lipoprotein metabolism. The invention also concerns the preparation and use in therapy of said recombinant viruses, especially in the treatment or prevention of dyslipoproteinemia-related pathologies. The method and apparatus of this invention consist of treating gum disease and include a light-producing dental appliance that is accessible exteriorly to the body for placement within the mouth of the patient to expose the mouth to light radiation of a selected wavelength and in an amount that is effective for killing or debilitating pathogenic microorganisms, especially *Porphyromona gingivalis* within the mouth of the patient such that the bacterial load carried to the heart is diminished, thereby reducing or eliminating the symptoms of coronary artery disease, atherosclerosis vascular inflammation, and plaque formation. The light source may comprise a laser, a source of ultraviolet light such as a low-pressure mercury lamp, a source of visible light such as an incandescent lamp, a flash lamp such as a xenon flash lamp, an arc lamp, a combination mercury-xenon lamp, an Excimer laser, a tunable dye laser, a laser diode, or a light-emitting diode (LED).

U.S. Pat. No. 6,962,585 issued in 2005 to L. Poleo, Jr. describes a catherization system and method for using an artery-blockage-removal system, including a hollow plastic tube with IR optical fibers extending longitudinally between its inner and outer walls. The catherization process includes the following steps: X-Ray dye is injected into an artery to pinpoint the location of a blockage; a guide wire of the catherization system is inserted into the artery to cross the location of the blockage; the catherization system is advanced along the guide wire to abut the blockage; IR and vacuum sources are activated, respectively, to dislodge the blockage from the artery walls and to remove arterial debris without damage to the artery and without risk of debris entering the blood stream.

However, laser treatment becomes especially problematic when it relates to cerebral arteries because intraluminal use of laser radiation, especially in coronary or cerebral blood vessels, is associated with the possibility of perforation of or thermal damage to the vessel walls and surrounding tissue. Accordingly, intravascular recanalization of occluded blood vessels is still an experimental procedure.

Recently, investigators have reported the use of continuous wave (CW) argon, neodymium-YAL, and carbon dioxide laser sources to successfully vaporize, coagulate, and penetrate atherosclerotic plaque in animals and in sections of coronary arteries taken from human cadavers. However, the investigators also report perforation of the vessel walls in many cases, particularly at laser energy levels that have been increased to a level sufficient to effect vaporization of plaque. That may occur because of inaccurate positioning of the end face of the optical fiber from the plaque and because the selected distance is not correlated with laser power.

Such laser energy levels are appropriately characterized as the "thermal" mode of laser operation that involves damage to tissue by virtue of heat accumulation in the tissue impinged by the laser radiation. Excessive heat accumulation causes thermal degradation or thermal necrosis. In other words, the temperature of the tissue rises, tissue proteins are denatured, and ultimately the tissue is coagulated and "evaporated" or "vaporized." While the laser thermal energy mode is effective in coagulating and vaporizing many tissues, including the tissues forming atherosclerotic plaques and senses, its use by the methods known heretofore in occluded coronary and cerebral blood vessels, for example, is not sufficiently safe and controllable. Consequently, the problem of inadvertent damage to or destruction of surrounding vessel tissue has been a major obstacle in the development of an acceptable microsurgical technique for laser angioplasty in the human vascular system.

U.S. Pat. No. 5,041,108 issued in 1991 to K. Fox, et al., discloses an attempt to solve the problems existing in laser cerebral endovascular treatment by providing a flexible catheter having an outside diameter of approximately 1.2 to 5.0 millimeters, which is especially suitable for use in coronary, cerebral, and somewhat larger carotid blood vessels, for example, to remove occlusions such as athermanous plaques. Within the catheter sheath are optical fibers and fluid channels. In one embodiment, the optical fibers include a bundle of laser-transmitting fibers eccentrically arranged relative to the catheter axis and radially movable toward that axis by means of a balloon positioned within the catheter sheath. Each laser fiber has a distal lens system which converges and cants the radiation beam away from the circumference of the catheter and toward the axis thereof. Alternate embodiments of the catheter include distal lens systems for laser fibers that may comprise one or more diverging lenses for special applications or techniques to be hereinafter described.

Fluid systems within the catheter include an outflow or suction channel for removal of fluids and debris and two or more inflow channels for injection of saline, pharmacologic agents, radio-opaque positioning dyes, immuno-specific antibodies, and the like. Carbon dioxide gas channels are also provided for inflation or deflation of both the laser-aiming balloon and a balloon circumferentially disposed about the catheter adjacent to the distal end thereof for occluding the vascular lumen and for establishing stabilization of the catheter distal end relative to said lumen.

A laser microsurgical system is operatively connected to the proximal end of the flexible angiographic catheter and comprises a proximal optical and fluid coupler for interconnecting the optical fibers and fluid channels of the catheter to the various system components, such as the laser apparatus and control, fiberoptical laser scanner, illumination and visualization systems, positioning systems, and fluid systems. The objects of the aforementioned invention are accomplished according to its method aspects by the use of visible light laser energy in the wavelength range of 351 to 515 nanometers, and, preferably, the blue-green emission lines at wavelengths of 488 and 514 nanometers from an argon-ion laser with a peak power output of about 20 W, such as a Spectra-Physics 171 Laser. The argon laser apparatus is operated in the pulsed or nonconducting mode using a pulse width or duration in the range of 5 to 200 milliseconds and a pulse repetition rate of 1 to 50 pulses per second with a duty cycle between 5 and 50%. The preferred pulse energy is in the range of 150 to 500 millijoules. Spot size for each fiber in the laser fiber bundle may be from 100 to 500 microns, preferably, the largest possible spot size in that range that is compatible with energy density requirements. The above parameters of pulsed laser energy are selected to effect damage to a luminal obstruction with substantially no thermal necrosis of the surrounding tissue.

However, the catheters used for the above methods have a complicated construction and are difficult to operate. Further-more, they cannot operate with lasers of high power and do not possess sufficient reliability.

OBJECTS AND SUMMARY OF THE INVENTION

It is an object of the present invention to provide such a surgical method for transluminal laser revascularization of cerebral blood vessels affected by atherosclerotic lesions that results in restoration of the entire diameter of the treated section of the vessel as well as unimpeded blood flow rate through the aforementioned section. It is another object to regenerate those functions of a patient's brain patient lost as a result of a stroke, as well as to regenerate locomotive, visual, congenital, intellectual, and other functions.

The method of the invention consists of the following steps: conducting preoperative examination of a patient suffering from atherosclerotic lesions by means of computerized and magnetic resonance tomography of the brain, scintography, angiography, rheography, etc., and defining arteries and capillaries of the brain affected by atherosclerosis; preparing a microcatheter or a set consisting of a plurality (three or more and up to six) of microcatheters for sequential coaxial insertion one into another and for guiding though the cerebral blood vessels to the affected zone; if necessary, modifying the distal tips of the catheters of the set in accordance with the shape of specific curves in the angioarchitectonica of the brain of the patient who is to be treated; conducting puncturing and catheterization for installing an introducer, e.g., into the common femoral artery; sequentially inserting one, two, or more microcatheters of the aforementioned set until the occluded portion of the affected coronary blood vessel is reached; inserting a light-guiding optical-fiber device coaxially into the innermost catheter; guiding the optical-fiber device to the affected zone through the innermost catheter; and conducting laser treatment of the affected zone with a high-energy laser operating in pulsedmode for removal of occlusive plaques from the inner walls of the vessel. The energy of the laser should exceed 20 W and should preferably be in the range of 20 to 35 W. The specific light source used in the method of the present invention is a YAL-type of laser operating on second harmonics with a wavelength of 539 nm. The laser source of this type is highly reliable and develops high power in the aforementioned range.

The catheters are radio-opaque, and the entire surgical intervention is carried out under constant X-ray TV observation. Laser treatment is accompanied by introduction of a heparinizated physiological solution.

After installation of the light-guiding optical-fiber laser device is completed, the catheter device is shifted and positioned in the descending arch of the aorta, and the inner catheter, or catheters, is shifted and positioned in the proximal part of the common carotid artery. Following this, the distance required for effective treatment is determined between the distal end face of the lightguide and the irradiated surface. This distance should be in the range of 1 to 5 mm. Laser treatment is then carried out by means of a high-energy laser having power not less than 20 W, i.e., in the range of 20 to 35 W, with advancement of the light-guiding device along the blood vessel together with the lightguide. A radio-opaque substance is periodically introduced for X-ray TV control of the treatment process.

The atherosclerotic tissues are destroyed primarily by photochemical treatment that results in the formation of small particles of debris having dimensions of 1.5 to 3 μm which can pass through capillaries and can be naturally removed without embolization in or occlusion of the distal bloodstream.

After completion of cerebral transluminal laser revascularization, conditions of the patient are checked by conducting cerebral angiograpy, the results of which are used to evaluate the degree to which the bloodstream is restored through the affected zone and the degree to which the lumen is dilated. If the first attempt fails to restore the lumen completely, the procedure is repeated.

If the results are successful and the passage through the bloodstream is completely restored, the catheter device and the introducer are removed, hemostasis is carried out, a compressive aseptic bandage is applied, and the patient is transferred to a postoperative ward where EKG (electrocardiogram) and EEG (electroencephalogram) monitoring are performed and where the patient is under observation by the medical staff.

The device for carrying out the method may comprise a three-way microcatheter device which is described in pending U.S. patent application Ser. No. 11/650,364 filed by the same applicant on Jan. 1, 2007 and which is incorporated herein by reference. The device has at its proximal end a three-way connection unit with one channel for coaxial insertion of microcatheters and a sealed lightguide insertable into the innermost catheter, and another channel for injection of a physiological solution. The device is provided with a plurality (usually, three to six) of individual catheters having gradually diminishing diameters for sequential coaxial insertion of one into the other. The individual microcatheters are unique in that their distal ends have a shape memory and are modified and tailored to specific and preliminarily determined angioarchitechtonica of the brain of the patient who is to be treated.

DETAILED DESCRIPTION OF THE INVENTION

Prior to surgical endovascular laser treatment, the patient is subjected to preoperative examination, which may include computerized and magnetic resonance tomography of the brain, scintography, rheography, and brain angiography.

The method of the invention for transluminal laser revascularization of the brain having atherosclerotic lesions consists of the following. First, preoperative examination of a patient suffering from atherosclerotic lesions is carried out with the use of computerized and magnetic resonance tomography of the brain, scintography, rheography, etc. The examinations define those arteries and capillaries of the brain that are affected by atherosclerosis.

A special microcatheter device of the type disclosed in pending U.S. patent application Ser. No 11/650,346 of the same applicant is prepared and consists of a set of microcatheters for sequential coaxial insertion one into another and for guiding though the cerebral blood vessels to the affected zone. If necessary, distal tips of the catheters are modified in accordance with the shape of specific curves in the angioarchitectonica of the brain of the patient who is to be treated.

At the next step, puncturing and catheterization is carried out in accordance with Seldinger's technique for installing an introducer, e.g., into the common femoral artery. The introducer may have a diameter of 4 F to 9 F and is sequentially used for inserting a first guiding catheter that comprises a hollow X-ray-opaque thin-walled reinforced tube with a modulated distal end. Two or more microcatheters of the aforementioned set are then coaxially inserted one into the other until the occluded portion of the affected coronary blood vessel is reached.

A light-guiding optical-fiber device is inserted into the innermost guiding catheter of the aforementioned set and is positioned close to the occluded area. The light-guiding optical-fiber device comprises a flexible X-ray-opaque catheter having a diameter of 3 F to 6 F. This catheter contains in its interior a slidingly installed quartz-quartz or quartz-polymer type of lightguide with the diameter of the optical fiber in the range of 100 to 200 μm. The lightguide is connected to a laser source.

At its proximal end, the catheter device is provided with a three-way connector, one channel of which is used to connect an injector for the supply of a heparinizated physiological solution into the treatment area, while another channel is used to insert the guiding catheter and the light-guiding device. The heparinizated physiological solution is introduced in an amount of not less than 0.1 ED of heparin per 1 ml of the physiological solution at a rate of no less than 1 ml/sec. The solution is needed for permanently washing the distal end face of the lightguide and for removing blood from the laser treatment area.

After installation of the first microcatheter, a second microcatheter is coaxially inserted into the first microcatheter, the third microcatheter is inserted into the second microcatheter, and, if necessary, other smaller-diameter microcatheters are sequentially inserted one into the other.

After installation of the light-guiding optical-fiber device, the guiding catheter device is shifted to the descending part of the aortic arch or to the proximal part of the common carotid artery, and then the distance required for effective treatment is determined between the distal end face of the lightguide and the laser-radiated surface. It is recommended that this distance range from 1 to 5 mm. The actual distance is selected by moving the light-guiding optical fiber relative to the treated object under X-ray observation in order to position the distal end face of the optical fiber at a distance that provides the optimal angle of divergence of the laser beam to cover the object while preventing damage to healthy blood vessel walls.

Following this, the affected zone is treated with a high-energy laser having power of no less than 20 W, e.g., in the range of 20 to 35 W and operation is carried out in pulsed mode. The specific light source used in the method of the present invention was a YAL-type of laser operating on a second harmonics with a wavelength of 539 nm. The laser source of this type appears to be highly reliable and develops high power in the aforementioned range.

The treatment is carried out simultaneously with the supply of a radio-opaque substance which is periodically introduced to the operation area for X-ray TV control of the treatment process.

The atherosclerotic tissues are destroyed primarily by photochemical treatment that results in the formation of small floating particles of debris having dimensions of 1.5 to 3 μm that can pass through the capillaries and that can be naturally removed without embolization in or occlusion of the distal blood vessels.

After completion of cerebral transluminal laser revascularization, conditions of the patient are checked by conducting cerebral angiograpy, the results of which are used to evaluate the degree to which the bloodstream is restored through the affected zone and the degree to which the lumen is dilated.

If the first attempt of transluminal laser revascularization of the affected coronary blood vessel fails to restore the lumen completely, the procedure is repeated.

If the results are successful and the passage through the bloodstream is completely restored, the catheter device and the introducer are removed, hemostasis is carried out, a compressive aseptic bandage is applied, and the patient is transferred to a postoperative ward where EKG (electrocardiogram) and EEG (electroencephalogram) monitoring are performed and where the patient is under observation by the medical staff.

The method of the invention is further described in more detail with reference to the examples given below.

EXAMPLE 1

Patient C, 56 years old, had an extensive stroke in the right hemisphere of the brain that led to left-side hemiparesis, caused speech disturbance, and developed distinct ear noise.

The preoperative examination included computerized tomography and magnetic resonance tomography of the brain, scintography, rheography, and brain angiography.

The computerized and magnetic resonance tomography revealed an extensive postischemic cyst of the right hemisphere. Scintography determined a slow-down in cerebral blood flow through the right hemisphere. Rheography showed a decrease of pulse volume in the right-side carotid sinuses. The brain angiography showed subtotal stenosis of the right medial cerebral artery trunk.

Operative surgical intervention was carried out 6 months after the stroke. The operation was carried out under roentgenoscopy. Puncturing and catheterization were carried out in accordance with the Seldinger's technique. A 8F introducer was installed, and a first catheter was guided through the introducer and selectively shifted to the place of origin of the right medial cerebral artery. The second microcatheter was coaxially inserted into the first one, the third microcatheter was coaxially inserted into the second one, etc. The catheters comprised thin-walled tubes made from an X-ray-opaque material of which the innermost material has a modulated distal end. The optical fiber lightguide device was then coaxially inserted into the innermost catheter and moved therethrough to the place of subtotal stenosis of the lumen. The optical fiber lightguide device had a flexible X-ray-opaque catheter of a 3 F diameter with a flexible quartz-quartz type of lightguide slidingly inserted into the aforementioned catheter. The light-guiding optical fiber had a diameter of 100 μm. The laser power source was a YAL-type laser operating on a second harmonics with a wavelength of 539 nm. The laser power was 32 W.

After installation of the light-guiding optical-fiber device, the guiding catheter device was shifted and positioned in the descending arch of the aorta, and the 3-mm distance was established between the distal end face of the lightguide and the surface of the atherosclerotic tissues to be irradiated by the laser as the distance that provided the optimal angle of divergence of the laser beam for covering the plaque while preventing damage to the healthy blood vessel walls. The atherosclerotic tissues were then subjected to laser treatment with the laser working in a pulse mode at a power of 32 W.

The operation was accompanied by introduction of a heparinizated physiological solution in an amount of 0.2 ED of heparin per 1 ml of the physiological solution at a rate of no less than 1.5 ml/sec. The solution was used for permanently washing the distal end face of the lightguide and for removal of blood from the laser treatment area. A radio-opaque substance (OmniPak 350) was periodically introduced for X-ray TV control and observation of deterioration of atherosclerotic tissues.

After operative intervention, the patient was subjected to a repeated cerebral angiography that confirmed a successful operation, destruction of the atherosclerotic tissue, and restoration of the bloodstream through the blood vessels.

The catheter and the introducer were extracted, hemostasis was carried out, and a compressive aseptic bandage was applied. The patient was transferred to a postoperative ward.

After passage of a predetermined period of time, the patient was subjected to repeated computerized and magnetic resonance tomography, scintograph, and REG. Results of the tests showed decrease in dimensions of the postischemic cyst of the right hemisphere, revealed improved blood flow, and improved rheographic characteristics in sinuses of the carotid arteries. Range of motion for the left hand and left leg was restored. Speech and intellectual abilities of the patient were restored as well, and the patient was able to return to his normal working activity.

EXAMPLE 2

Patient T, 43 years old, had an extensive stroke in the left hemisphere of the brain. The preoperative examination was conducted in accordance with the same scheme as in Example 1. The examination revealed an extensive postischemic cyst of the left hemisphere, a slow-down in cerebral blood flow through the left hemisphere, a decrease of pulse volume in the left side of the brain, and occlusion of the left cerebral artery trunk.

Operative surgical intervention was carried out 12 months after the stroke with the same operative steps and sequences described in Example 1.

Catheterization was carried out through the common femoral artery with installation of a 8 F introducer used for insertion of a guiding catheter. The catheter was guided to and super-selectively positioned relative to the left anterior cerebral artery. The second microcatheter was coaxially inserted into the first one, the third microcatheter was coaxially inserted into the second one, etc. The catheters comprised thin-walled tubes made from an X-ray-opaque material of which the innermost material has a modulated distal end. The optical-fiber lightguide device was then coaxially inserted into the innermost catheter and moved therethrough to the place of subtotal stenosis of the lumen. The optical-fiber lightguide device had a flexible X-ray-opaque catheter of a 3 F diameter with a flexible quartz-polymer type of lightguide slidingly inserted into the aforementioned catheter. The light-guiding optical fiber had a diameter of 150 μm. The laser power source was the same as in Example 1.

The operation was accompanied by introduction of a heparinizated physiological solution in an amount of 0.2 ED of heparin per 1 ml of the physiological solution at a rate of 2 ml/sec.

After operative intervention, the patient was subjected to a repeated cerebral angiography that confirmed that the operation was successful, atherosclerotic tissue were destructed, and the bloodstream through the blood vessel was restored.

Thus, it has been shown that the method of the present invention makes it possible to regenerate the structure of cerebral tissue, to develop regeneration processes of brain structures, and to restore locomotive activity, vision, memory, and intellectual ability of patients suffering from atherosclerotic lesions of the brain.

The invention claimed is:

1. A method of transluminal laser revascularization of cerebral blood vessels having atherosclerotic lesions comprising the steps of:
    conducting preoperative examination of the patient for detecting cerebral blood vessels affected by atherosclerotic lesions;
    providing a microcatheter device comprising at least a first channel and a second channel, a plurality of microcatheters of gradually reducing diameters for coaxial insertion one into another through the first channel, a light-guiding optical-fiber device connected to a high-power laser source and insertable into the innermost of said plurality of microcatheters, and a source of a washing liquid for supply into the area being treated through the second channel;
    puncturing and catheterizing the common femoral artery of the patient for installing an introducer;
    inserting a first microcatheter of said plurality of microcatheters into the introducer;
    coaxially inserting and moving forward a second microcatheter of said plurality of micorcatheters into the first microcatheter;
    coaxially inserting and moving forward a third microcatheter of said plurality of micorcatheters into the second microcatheter;
    if necessary, sequentially inserting and moving forward other microcatheters of said plurality of microcatheters into the preceding microcatheter until reaching the affected zone of the microcirculation bloodstream in the patient's brain;
    inserting the light-guiding optical-fiber device coaxially into the innermost catheter of said plurality of microcatheters;
    guiding the light-guiding optical-fiber device to the zone of the blood vessel occluded by the atherosclerotic lesion;
    shifting the catheter device to the descending arch of the aorta or the proximal part of the common carotid artery;
    adjusting the distance from the tissue affected by atherosclerotic lesion to the distal end face of the optical fiber device that provides the optimal angle of divergence of the laser beam for covering the tissue affected by atherosclerotic lesions while preventing damage to healthy blood vessel walls; and
    restoring the circulation and bloodstream through the treated cerebral blood vessel by conducting laser treatment of the affected tissue, the aforementioned microcatheters being made from a radio-opaque material and said laser treatment being carried out under X-ray TV observation.

2. The method of claim 1, wherein the aforementioned laser has a power in the range of 20 to 35 W, said laser treatment being carried out in a pulsed mode.

3. The method of claim 1, wherein the distance from the tissue affected by atherosclerotic lesion to the distal end face of the optical fiber device is in the range of 1 to 5 mm.

4. The method of claim 2, wherein the distance from the tissue affected by atherosclerotic lesion to the distal end face of the optical fiber device is in the range of 1 to 5 mm.

5. The method of claim 1, wherein said plurality of microcatheters are three to six microcatheters.

6. The method of claim 2, wherein said plurality of microcatheters are three to six microcatheters.

7. The method of claim 3, wherein said plurality of microcatheters are three to six microcatheters.

8. The method of claim 1, wherein said plurality of microcatheters have distal ends with a shape memorized by shape memory and wherein said shape corresponds to the angioarchitechtonica defined in said step of preoperative examination of the patient.

9. The method of claim 2, wherein said plurality of microcatheters have distal ends with a shape memorized by shape memory and wherein said shape corresponds to the angioarchitechtonica defined in said step of preoperative examination of the patient.

10. The method of claim 3, wherein said plurality of microcatheters have distal ends with a shape memorized by shape memory and wherein said shape corresponds to the angioarchitechtonica defined in said step of preoperative examination of the patient.

11. The method of claim 1, wherein the washing liquid is a heparinizated physiological solution.

12. The method of claim 3, wherein the washing liquid is a heparinizated physiological solution.

13. The method of claim 9, wherein the washing liquid is a heparinizated physiological solution.

14. The method of claim 10, wherein the washing liquid is a heparinizated physiological solution.

15. The method of claim 2, wherein the light source is a YAL-type of laser operating on second harmonics with a wavelength of 539 nm.

16. The method of claim 4, wherein the light source is a YAL-type of laser operating on second harmonics with a wavelength of 539 nm.

17. The method of claim 7, wherein the light source is a YAL-type of laser operating on second harmonics with a wavelength of 539 nm.

18. The method of claim 10, wherein the light source is a YAL-type of laser operating on second harmonics with a wavelength of 539 nm.

* * * * *